US00PP10300P

United States Patent [19]

Cosner et al.

[11] Patent Number: Plant 10,300

[45] Date of Patent: Mar. 24, 1998

[54] NEW GUINEA IMPATIENS PLANT NAMED 'ELECTRA ROYALE'

[76] Inventors: Harlan B. Cosner; Sue L. Cosner, both of P.O. Box 173, Broadbent, Oreg. 97414

[21] Appl. No.: 772,108

[22] Filed: Dec. 23, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Electra Royale', characterized by its numerous, large, rounded purple flowers; flowers held above the foliage; freely branching, dense and bushy plant habit; moderately vigorous and compact, rounded, almost spherical plant habit; and dark green and glossy foliage.

1 Drawing Sheet

The present invention relates to a new and distinct cultivar of New Guinea Impatiens plant, botanically known as *Impatiens hawkeri*, and hereinafter referred to by the cultivar name 'Electra Royale'.

The new cultivar is a product of a planned breeding program conducted by the inventors in Coquille, Oreg. The objective of the breeding program was to develop varieties with uniform plant habit, attractive flower colors, good flower form, and numerous flowers per plant.

The new cultivar originated from a cross made in Feb., 1994, by the inventors of two unnamed proprietary seedling selections.

The cultivar 'Electra Royale' was discovered and selected by the inventors as a flowering plant within the progeny of the stated cross in a controlled environment in Coquille, Oreg. Asexual reproduction of the new cultivar by terminal cuttings taken at Coquille, Oreg. has shown that the unique features of this new New Guinea Impatiens are stable and reproduced true to type in successive generations of asexual reproduction.

The following traits have been repeatedly observed and are determined to be the unique characteristics of 'Electra Royale'. These characteristics in combination distinguish the new New Guinea Impatiens as a new and distinct cultivar:

1. Large purple flowers.
2. Flowers held above the foliage.
3. Rounded flower form.
4. Numerous flowers per plant.
5. Freely branching, dense and bushy plant habit.
6. Moderately vigorous and compact, rounded, almost spherical plant habit.
7. Dark green and glossy foliage.

In contrast to plants of the new New Guinea Impatiens, plants of the male proprietary seedling selection are taller, not as freely branching, have larger leaves and fewer flowers.

In contrast to plants of the new New Guinea Impatiens, plants of the female proprietary seedling selection have smaller flowers and flower color is red.

The new New Guinea Impatiens is similar in flower color to the New Guinea Impatiens cultivar 'Papete' (disclosed in U.S. Plant Pat. No. 8,457). However in side-by-side comparisons in Coquille, Oreg., under commercial practice, plants of the new New Guinea Impatiens differed from plants of the cultivar 'Papete' in the following characteristics:

1. Plants of the new New Guinea Impatiens are rounded in plant shape whereas plants of the cultivar 'Papete' are more upright.

2. Stem color of plants of the new New Guinea Impatiens is green with red tones whereas stem color of plants of the cultivar 'Papete' is red.
3. Plants of the new New Guinea Impatiens flower about 1.5 weeks earlier than flowers of plants of the cultivar 'Papete'.
4. Plants of the new New Guinea Impatiens have more flowers per lateral stem than of plants of the cultivar 'Papete'.
5. Flowers of plants of the new New Guinea Impatiens are displayed above the foliage whereas flowers of plants of the cultivar 'Papete' are often down in the foliage.
6. Flowers of plants of the new New Guinea Impatiens are larger than flowers of plants of the cultivar 'Papete'.
7. Flowers of plants of the new New Guinea Impatiens are round in shape with petals overlapping whereas flowers of plants of the cultivar 'Papete' are star-shaped with gaps between the petals.

A detailed comparison of plants of the new New Guinea Impatiens and the cultivar 'Papete' appears in Chart A at the end of the specification.

The new New Guinea Impatiens has not been observed under all possible environmental conditions. The phenotype may vary significantly with variations in environment such as temperature and light level, without, however, any variance in genotype.

The accompanying colored photographs illustrate the overall appearance and flower color of the new New Guinea Impatiens, showing the colors as true as it is reasonably possible to obtain in colored reproductions of this type.

The first photograph comprises a side perspective view of a typical plant of the new New Guinea Impatiens.

The second photograph comprises a side perspective view of typical plants of the cultivar 'Papete' (left) and the new New Guinea Impatiens (right) showing the differences in plant and flowering habit.

Flower and foliage colors in the photographs may appear different from the actual colors due to light reflectance.

The following observations, measurements, values, and comparisons describe plants grown in Coquille, Oreg., grown under double layer of polyethylene with day temperatures ranging from 23 to 30C. and night temperatures ranging from 10 to 18C., and light levels ranging from 3,000 to 5,000 footcandles.

In the following description, color references are made to The Royal Horticultural Society Colour Chart except where general terms of ordinary dictionary significance are used.

Botanical classification: *Impatiens hawkeri* cultivar 'Electra Royale'.

Parentage:

*Male or pollen parent.*—Unnamed proprietary seedling selection.

*Female or seed parent.*—Unnamed proprietary seedling selection.

Propagation:

*Type cutting.*—Terminal cuttings.

*Time to initiate roots.*—About 24 days at a temperature of 20C.

*Rooting habit.*—Numerous, fibrous, and well-branched.

Plant description:

*Form.*—Rounded, almost spherical plant form.

*Growth habit.*—Moderately vigorous and compact. Freely branching, dense ad bushy growth. Flowers above or beyond the foliage. Suitable for 10 to 25-cm containers. Leaves horizontal to plant.

*Plant height.*—About 16 cm.

*Lateral branches.*—Size: Length: About 11 cm. Diameter: About 7 mm. Color: 146A with red, 59A, tones.

*Foliage description.*—Leaves simple, generally symmetrical, abundant, opposite or in whorls of three, horizontal to plant and flat in aspect. Size, largest leaves: Length: About 8 cm. Width: About 3 cm. Shape: Ovate with acuminate apex, attenuate base and ciliate margin. Texture: Smooth, glossy. Color: Upper surface: 147A. Lower surface: 147B. Venation, upper surface: 147B, red at proximal end. Venation, lower surface: 59A. Petiole: Size: Length: About 1.3 cm. Diameter: About 3.5 mm. Color: Lighter than 59A.

Flower description:

*Flower type and habit.*—Large purple flowers. Freely and continuously flowering. Flowers arise from leaf axils. Usually six flowers per lateral branch. Flowers positioned above or beyond the foliage and face upward or outward. Flowers flat and rounded. Flowers self-cleaning.

*Time to flower.*—Flowering generally commences four to six weeks after planting.

*Flowering season.*—Year-round under greenhouse conditions. In the garden, flowering is continuous from spring until fall.

*Flower size.*—Length: About 6 cm. Width: About 6.5 cm. Depth: About 3.5 mm.

*Flower buds.*—Size: Length: About 1.7 cm. Diameter: About 1 cm. Shape: Ovoid. Color: 74B.

*Petals.*—Size (largest petals): Length: Top petal: About 2.5 cm. Middle petals: About 3.25 cm. Bottom petals: About 3 cm. Width: Top petal: About 4 cm. Middle petals: About 3 cm. Bottom petals: About 3.5 cm. Shape: Cordate with emarginate apex, cuneate or obtuse base and entire margin. Texture: Velvety, smooth. Color: When opening, upper surface: Iridescent, 74A. When opening, lower surface: Iridescent, 74B. Mature, upper surface: Iridescent, 74A. Mature, lower surface: Iridescent, 74B. Fading to: Iridescent, 74A.

*Spur.*—Length: About 5 cm. Shape: Narrow and curved. Color: 59A.

*Peduncles.*—Length: About 4.5 cm. Angle: Upright. Strength: Strong. Color: 146B with 59A overtones.

*Reproductive organs.*—Androecium: Anther shape: Lobate. Anther size: About 5 mm. Anther color: 59A at base, white at apex. Amount of pollen: Moderate. Pollen color: White. Gynoecium: Stigma color: White. Style length: About 4 mm. Style color: Green. Ovary color: Green.

Disease resistance: Under commercial conditions, resistance nor susceptibility to pathogens has not been observed.

CHART A

| CHARACTERISTIC | ELECTRA ROYALE | PAPETE |
|---|---|---|
| PLANT SHAPE | Rounded, almost spherical | Upright |
| PLANT HEIGHT | About 16 cm | About 15 cm |
| LATERAL BRANCH LENGTH | About 11 cm | About 10 cm |
| LATERAL BRANCH DIAMETER | About 7 mm | About 7.5 mm |
| STEM COLOR | 146A with red (59A) tones | 59A |
| PETIOLE LENGTH | About 1.3 cm | About 1.5 cm |
| PETIOLE DIAMETER | About 3.5 cm | About 3 mm |
| PETIOLE COLOR | Light than 59A | 59A |
| FLOWER POSITION | Flowers above the foliage | Flowers down in the foliage |
| TIME TO FLOWER | 1.5 weeks before Papete | 1.5 weeks after Electra Royale |
| QUANTITY OF FLOWERS AND BUDS PER LATERAL STEM | About 6 | About 4 |
| FLOWER SHAPE | Rounded, petals overlapping | Star-shaped, gaps between petals |
| FLOWER SIZE | 6 by 6.5 cm | 5.5 by 5.5 cm |
| SPUR LENGTH | About 5 cm | About 5.5 cm |
| WHEN OPENING PETAL COLOR, UPPER SURFACE | 74A | 74B |
| WHEN OPENING PETAL COLOR, LOWER SURFACE | 74B | 74C |
| MATURE PETAL COLOR, UPPER SURFACE | 74A | 74B |
| MATURE PETAL COLOR, LOWER SURFACE | 74B | 74C |
| PEDUNCLE COLOR | 146B with 59A overtones | 59B with green overtones |

It is claimed:

1. A new and distinct New Guinea Impatiens plant named 'Electra Royale', as illustrated and described.

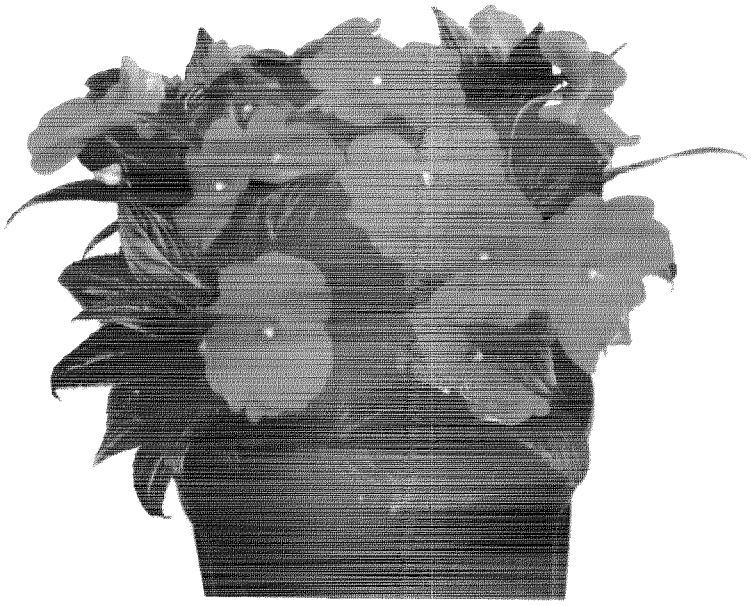
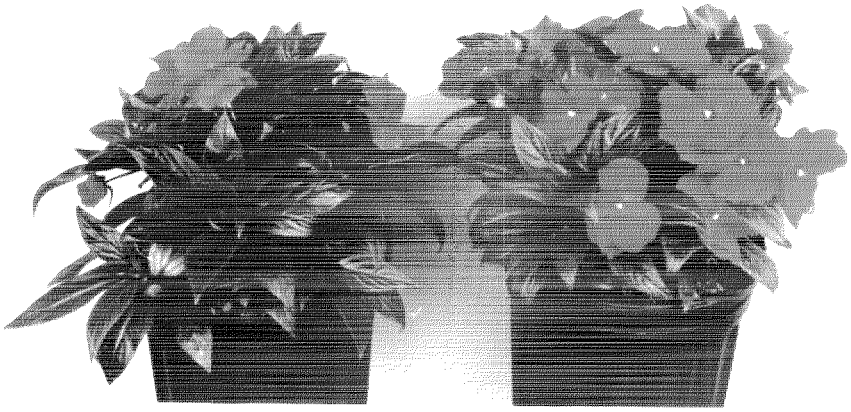

* * * * *